United States Patent [19]

Taylor et al.

[11] Patent Number: 5,684,300

[45] Date of Patent: Nov. 4, 1997

[54] CORONA DISCHARGE IONIZATION SOURCE

[76] Inventors: Stephen John Taylor, 2 Westfield, Hyde Heath, Amersham, Buckinghamshire HP6 5RE; Robert Brian Turner, 163 Chartridge Lane, Chesham, Buckinghamshire HP5 2SE; Paul Douglas Arnold, 33 Gloucester Road, Bedford MK42 9TL, all of Great Britain

[21] Appl. No.: 624,132

[22] Filed: Mar. 29, 1996

Related U.S. Application Data

[63] Continuation of Ser. No. 244,560, filed as PCT/GB92/02242, Dec. 3, 1992, abandoned.

[51] Int. Cl.⁶ .............................. G01D 55/44; H01J 49/40
[52] U.S. Cl. .............................. 250/286; 250/288
[58] Field of Search .............................. 250/324, 325, 250/326, 286, 287, 288; 361/229

[56] References Cited

U.S. PATENT DOCUMENTS

| | | | |
|---|---|---|---|
| 3,699,335 | 10/1972 | Giaimo | 250/326 |
| 4,100,411 | 7/1978 | Davis | 250/324 |
| 4,390,784 | 6/1983 | Browning et al. | 250/287 |
| 4,672,505 | 6/1987 | Tsuchiya et al. | 250/324 |
| 4,772,794 | 9/1988 | Jenkins | 250/283 |
| 5,070,240 | 12/1991 | Lee et al. | 250/286 |
| 5,162,652 | 11/1992 | Cohen et al. | 250/288 |

FOREIGN PATENT DOCUMENTS

62-163249  7/1987  Japan.

*Primary Examiner*—Bruce Anderson

[57] ABSTRACT

A corona discharge ionization source, for use for example with an ion mobility spectrometer, comprises an adjustable corona point electrode (20) which is held transversely within a cylindrical target electrode (14). A corona discharge is produced by a constant or pulsed potential difference between the two electrodes. In alternative embodiments, there may be a further corona discharge electrode (58), providing additional control, and also an annular counter-electrode (60) surrounding the further point electrode (58).

22 Claims, 8 Drawing Sheets

Typical high voltage pulse.

Gated positive ion spectrum.
DC corona

FIG. 5

Gated negative ion spectrum
DC corona

FIG. 6

Typical high voltage pulse.

FIG. 7

Typical ion pulse in positive ion mode.
System not gated

FIG. 8

Typical ion pulse in negative ion mode.
System not gated

FIG. 9

Typical positive ion mode, gated spectrum.
System nominally clean

FIG. 10

Typical negative ion mode, gated spectrum.
System nominally clean

FIG. 11

Positive ion mode.

FIG. 12

Negative ion mode.

FIG. 13

Negative ion mode.

CORONA DISCHARGE IONIZATION SOURCE

This application is a continuation of application Ser. No. 08/244,560 filed as PCT/GB92/02242, Dec. 3, 1992 which application is now abandoned.

The present invention relates to ionization sources for analytical instruments, more particularly corona discharge ionization sources, and to detectors and instruments employing such sources. The invention relates particularly but not exclusively to sources for ion mobility spectrometers.

The operation of a number of analytical instruments is dependent upon the ionization of either the separated or unseparated components of a material of interest, most usually a gas or vapour. In the case of already separated components this is followed by measurement of the respective resulting ionic current flows; or in the case of unseparated components, first by separation based upon the one or more characteristics of the resultant ions, followed by ionic current measurement of the respective separated ion groups.

The magnitude of the ionic currents in either case is an indication of the quantity of the individual separated components of the original material of interest.

An example of the first type of equipment is the gas chromatograph where time-separation of the components of a sample, by means of a separation column, precedes their introduction into a detector, for example an electron capture detector. An example of the second type of equipment is the ion mobility spectrometer where the ionized but unseperated components of a sample material are subsequently time-separated in a drift tube as a function of the respective ion mobilities. A further example of the second type is the mass spectrometer where the component ions are separated according to their ionic masses.

Ionization in such detectors or instruments is frequently achieved by means of the ionizing radiation emanating from a radioactive source, for example Nickel-63, which is commonly used as the ionizing material in both electron capture detectors and in ion mobility and mass spectrometers. The radioactive material is most usually deployed as a plating upon a metal foil, which may be formed into a cylindrical configuration through which the material to be ionized is passed.

The employment of radioactive source materials requires special precautions, and in many territories is subject to exhaustive regulatory controls for reasons of health end safety. Extensive precautions, and considerable associated documentation, are therefore required in the manufacture, transport, storage, use and repair of detectors end instruments incorporating such radioactive ionizing sources.

It is thus one object of the present invention to provide a non-radioactive ionizing source for use with such detectors and instruments, without the substantial disadvantages associated with the use of radioactive ionization sources.

A further object of the invention is the provision of detectors and instruments incorporating such non-radioactive ionizing sources.

A still further object is the provision of an ion-mobility spectrometer incorporating such a non-radioactive ionization source.

According to one aspect of the invention a non-radioactive ionization source of the type referred to consists in a corona discharge ionization source comprising a corona discharge electrode and a further, or target, electrode and means for applying a potential between the corona discharge electrode and the further, or target, electrode in order to establish a corona discharge between the two electrodes, hereby to ionize material introduced into the region of the discharge.

The potential applied between the corona discharge electrode and the further electrode to establish the corona discharge may be constant.

The potential applied between the two electrodes may alternatively be in the form of a pulse or pulses of magnitude sufficient to establish a corona discharge.

The pulse or pulses may be applied in addition to a constant potential which would not itself be sufficient to establish a corona discharge.

The magnitude and the repetition rate of the pulses may be varied in either case.

The constant potential applied to the corona discharge electrode may be negative or positive with respect to the further or target electrode, and the pulse or pulses negative-going or positive-going with respect to the further electrode.

Where a constant negative or positive potential below that necessary to establish a corona discharge is applied, the additional pulse or pulses to initiate corona discharge will be negative-going or positive-going, respectively.

The corona discharge electrode of the ionization source maybe in the form of a point, for example the tip of a metal wire. The wire may be coated or uncoated.

Alternatively the corona discharge electrode may be the tip of one or more carbon fibres.

Whilst it has been found that carbon fibre points are capable of stable operation in corona ionization sources to produce ions of the required type and in sufficient quantity, such carbon fibre points are self-consuming and may have an insufficiently long operating life for an instrument required to operate continuously.

Nevertheless sources employing carbon fibre points are considered to have considerable potential for application to intermittently operating instruments.

Metal wire discharge points used in such corona ionization sources have been found to have a far longer life in operation, but to operate with considerably less stability than carbon fibre points. In general it has been found that such metal discharge points can produce varying quantities of ions from identical energisations, and can have a discharge initiation potential which can vary subsantially from energisation to energisation.

From another aspect the invention may consist in a discrete ionization detector comprising an ionization source according to the invention.

From a further aspect the invention may consist in an ion mobility spectrometer incorporating an ionization source according to the invention.

The ion mobility spectrometer may but need not incorporate gating means for controlling the introduction into the drift tube of ions produced by the ionization source.

Where gating means are incorporated the gating means may be opened at a predetermined time after initiation of the corona discharge. Means may be provided for varying the time between initiation of the discharge and the opening of the gate.

Means may also be provided for adjusting the magnitudes of the potentials, both constant and pulse, whether applied alone or together, which initiate and maintain the corona discharge. Means may also be provided for varying the duration of the pulses.

According to another aspect of the invention an ionization source of the type referred to consists in a corona discharge ionization source comprising a first, corona discharge, electrode and a further, or target, electrode, and means for applying a potential between the corona discharge electrode and the further electrode in order to establish a corona discharge between the two electrodes, thereby to ionize material introduced into the region of the discharge, the source further comprising a second electrode in the region of the first, corona discharge electrode, and means for applying a potential to the second electrode of opposite sign to that applied to the first corona discharge electrode, in order to establish a corona discharge upon the second electrode.

Whilst the physical mechanisms involved are uncertain, although it is believed that the discharge upon the secondary point may "seed" the region of the first point with suitable charge carriers, it has been shown that provision of a corona ionization source incorporating the secondary corona discharge electrode enables the stability of operation of the primary discharge to be controlled, as well as enabling further control of the number of ions produced from the first electrode, by variation of the potential applied to the secondary electrode.

These and other aspects of the invention will be described, by way of example, with reference to the accompanying drawings, in which:

FIG. 1i bis a side view of the source of FIG. 1a;

Figure 1A:
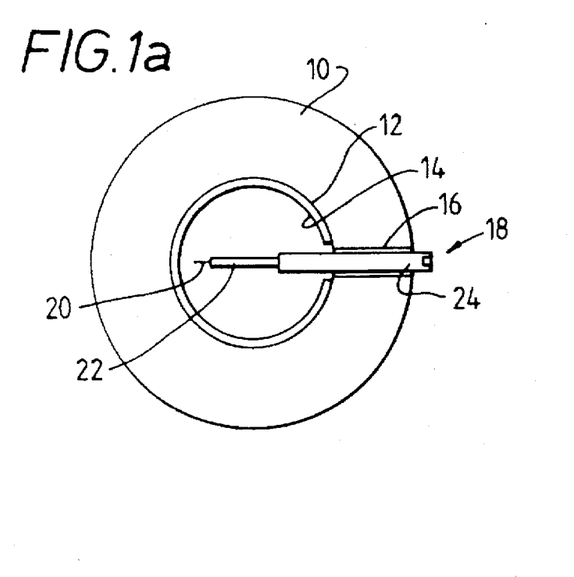
FIG. 1a is a plan view of a corona ionization-source in accordance with a first embodiment of the invention.

Referring to FIG. 1a a corona discharge source in accordance with the invention consists of an annular body 10 of PTFE with an outer diameter of 30 mm, an inner diameter of 14 mm and a length of 15 mm. An inner wall 12 of the body 10 carries a target electrode 14 of gold-plated brass with a longitudinal gap 16 through which a corona discharge point electrode assembly 18 projects.

The assembly 18 comprises a corona point 20, a conducting rod 22, and carrier 24 which mounts the assembly through an aperture 26 (FIG. 1b) in the wall of the annular body 10 and permits adjustment of the corona discharge gap between the corona point 20 and the target electrode 14.

Figure 1B:
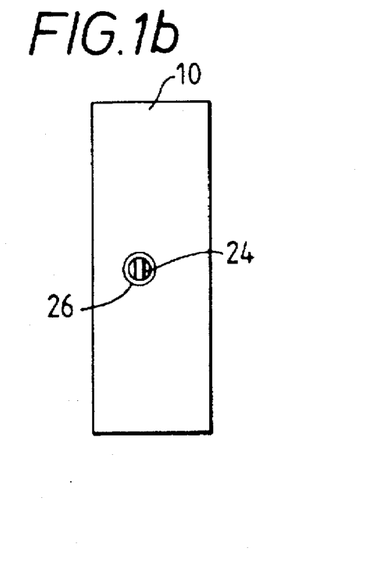

Electrical connections (not shown) are made to the corona point 20 and the target electrode 14 respectively to permit the application of an electrical potential between them.

Various materials may be employed for the corona point 20, for example, a 125 micron tinned copper wire, a 25 micron thoriated tungsten wire, a 13 micron molybdenum wire, and a 1 micron platinum wire. Also used has been a tuft of carbon fibres with an overall diameter of some 0.5 mm, drawn from a carbon fibre twine (Type C 005750) supplied by Goodfellows Advanced Materials, and an individual carbon fibre of some 1-2 microns diameter from the same twine.

Figure 2:
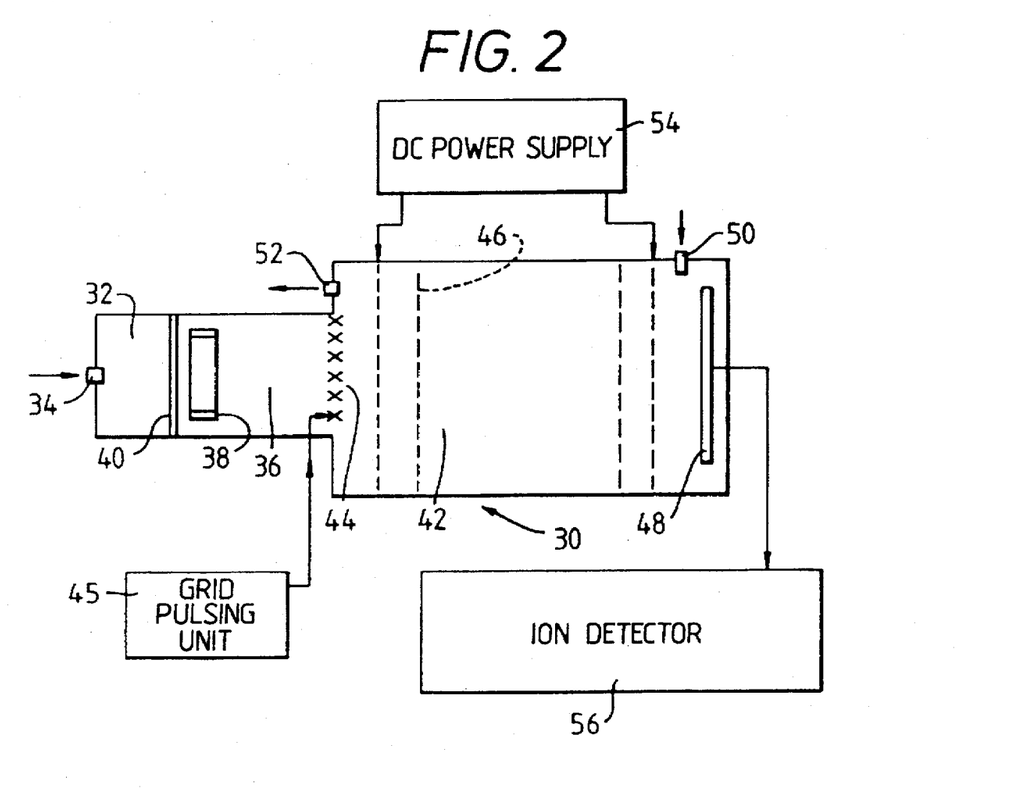
FIG. 2 is a partly schematic view showing the corona ionization source of FIG. 1 incorporated in an ion mobility spectrometer.

The most consistent performance has been obtained from the carbon fibre tuft corona point which was employed in the apparatus of FIG. 2 to produce the various spectra illustrated in the accompanying drawings.

FIG. 2 shows the corona ionization source of FIG. 1 assembled into an ion mobility spectrometer such as the CAM (RTM) chemical agent monitor, manufactured and sold by the applicants, in place of the Nickel-63 ionising source normally employed with that equipment.

The construction end operation of ion mobility spectrometers, which may also be referred to as plasma chromatographs, are well known in the art, and are described for example in "Plasma Chromatography" ed. T. W. Carr, Plenum Press (1984).

The ion mobility spectrometer of FIG. 2 includes a sample introduction chamber 32 into which sample material may be admitted through an inlet 34, the chamber 32 being separated from reaction chamber 36, containing a corona discharge ionization source 38, by a semi-permeable membrane 40 through which the sample material can diffuse. The sample molecules are ionized in the reaction chamber 36 by the corona discharge established within the ionization source 38 by the application to it of an appropriate potential or potentials. A proportion of the ions resulting from the ionization may be allowed into a drift tube portion 42 of the tube assembly by the application to a gating grid 44 or a pulse of potential from a unit 45, the duration of which determines the time for which the ions are able to pass into the drift tube 42.

The drift tube 42 includes a series of electrodes 46 to establish a uniform electrostatic field along its length so as to draw ions passed by the gating grid 44 towards a collector electrode 48. A drift gas flow is established in the drift e 42 by means of an inert gas which is introduced into the drift tube through a port 50 and exhausted through a port The electrodes 46 are fed from a high voltage DC power supply 54 with an appropriate series of DC potentials. Ions reaching the collector electrode 48 through the drift tube give rise to ionic current flows which may be detected by a unit 56 which may also include electronic circuitry for measuring, indicating, processing and storing information relating to the magnitude and time of arrival at the collector electrode 48 of ionic groups related to various components of the originally introduced sample. From these values it is possible to identify and quantify the amount of a particular material present in the original sample.

The corona discharge itself may be established by means of a steady DC potential, positive or negative; by means of unidirectional potential pulses, positive or negative; or by means of a steady DC potential, positive or negative, below the corona discharge threshold level, to which unidirectional pulses, positive-going or negative-going respectively are added to take,he applied potential above the threshold.

Figure 4:
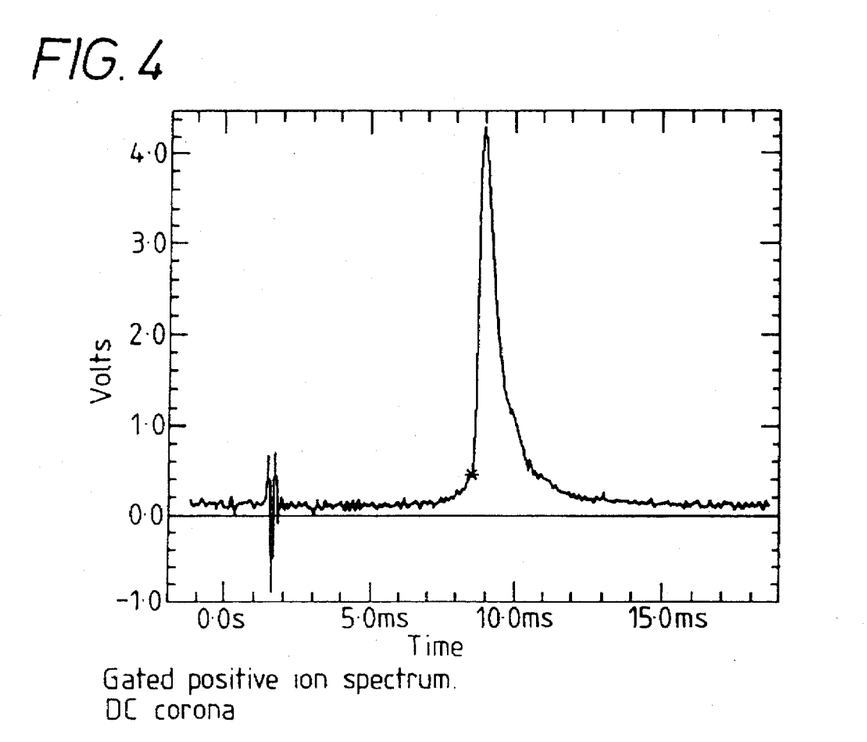
FIGS. 4, 5 and 7 to 13 are ion spectra obtained from the ion mobility spectrometer of FIG. 2, employing the corona ionization source of FIG. 1, under various operating conditions.

Using the apparatus of FIG. 2 with a positive DC potential typically of between 2 kV and 4 kV, i.e. in excess of the corona threshold of the source 38, and with the gating electrode 44 closed except for periods of 180 microseconds every 120 milliseconds, and with acetone doping of a circulating atmosphere of dry air, the positive ion spectrum shown in FIG. 4 was obtained.

Figure 5:
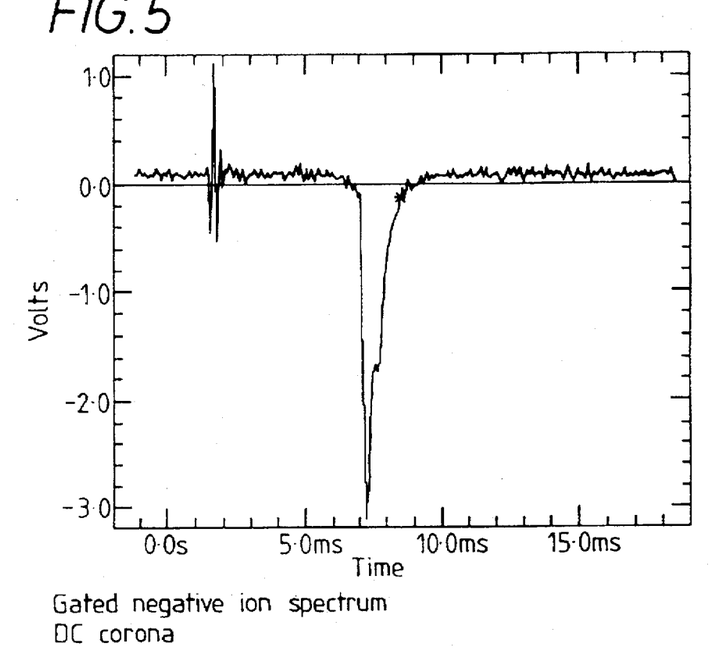

With a negative DC potential typically of between 2 kV and 4 kV, the same gating frequency and duration, the negative ion spectrum of FIG. 5 was obtained.

Both spectra indicate that a range of ions of significantly different mobilities are produced by the corona discharge ion source. In the absence of gating by the gating electrode 44, large ion flows into the drift tube 30 produce ion currents in both positive and negative modes of operation sufficient to cause saturation of the preamplifier in the external circuit of the collector 48.

Using the apparatus of FIG. 2 with a DC potential typically of between 1 kv and 2 kv, (i.e. below the corona discharge threshold of the source 38) a series of narrow high-voltage pulses sufficient when added to the DC potential to cause the discharge threshold to become exceeded, was further applied to the source, causing the discharge to be switched on and off rapidly, thereby reducing the energy density around the corona point and hence reducing the production of unwanted compounds in the ionisation region as a result of the discharge.

Figure 3:
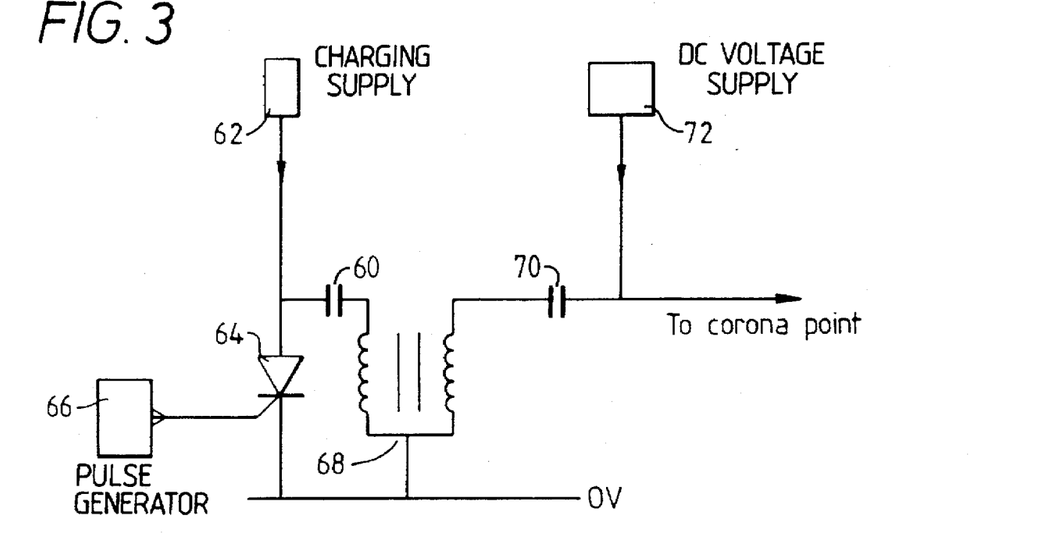
FIG. 3 is the circuit diagram of a high voltage pulse generator which may be employed with the corona ionization source of FIGS. 1 and 2.

The pulses were generated and applied to source 38 by means of the circuit shown in FIG. 3, comprising a discharge capacitor 60 charged from a charging supply able to discharge through thyristor 64 when the latter is switched on by means of a switching pulse from a pulse generator 66. The current flow through the primary winding of a step-up pulse transformer 68, produces a magnified voltage pulse across the secondary applied through a blocking capacitor 70 to the corona point of the source 38, to which a high voltage DC potential below the corona discharge potential is applied, from a supply 72.

Figure 6:
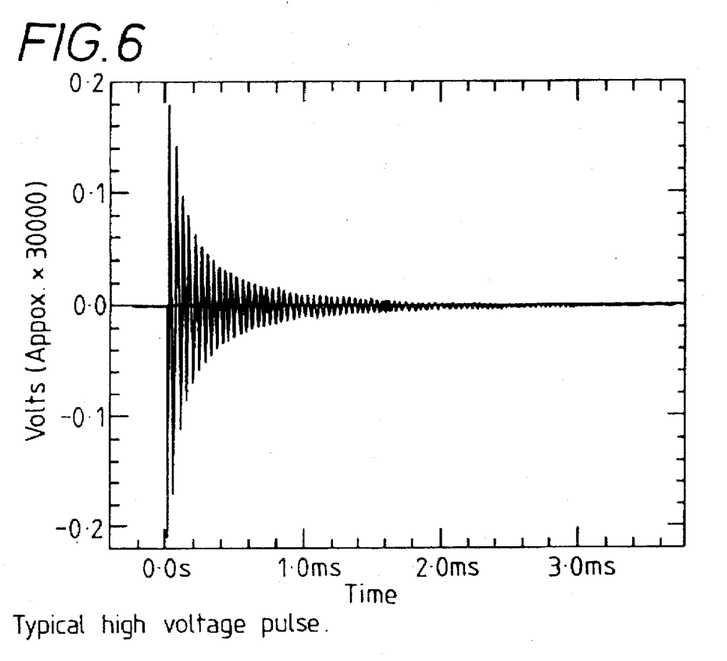
FIG. 6 is the waveform of the pulse produced by the circuit of FIG. 3.

The form of the high voltage pulse produced by the circuit of FIG. 3 is shown in FIG. 6. It will be appreciated that as the pulse consists of alternate positive and negative going excursions about a mean level, the same form of pulse may be used to switch either a negative or positive corona discharge, the polarity of the discharge being determined by the polarity of the potential applied to the corona point from the supply 72.

It was found that a range of DC potentials, typically 1 kV to 3 kV, positive and negative, and pulse voltages, typically 1 kV to 10 kV, would produce a short-lived corona discharge in the source 38, each successive pulse of the form shown in FIG. 6 causing a short discharge to occur.

Higher voltages were found necessary to establish and maintain the positive ion corona discharge then the negative one.

Figure 7:
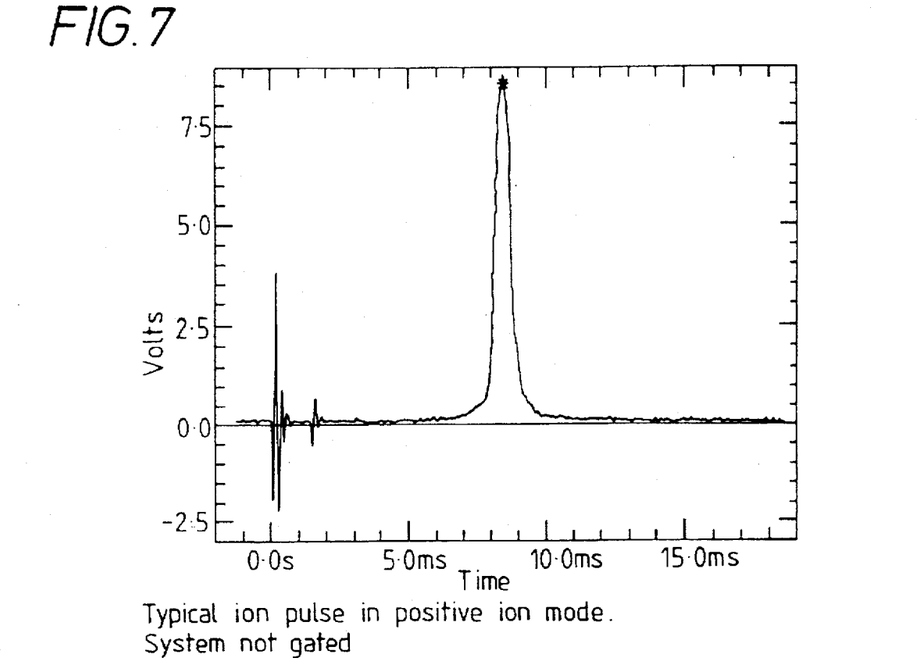
Figure 8:
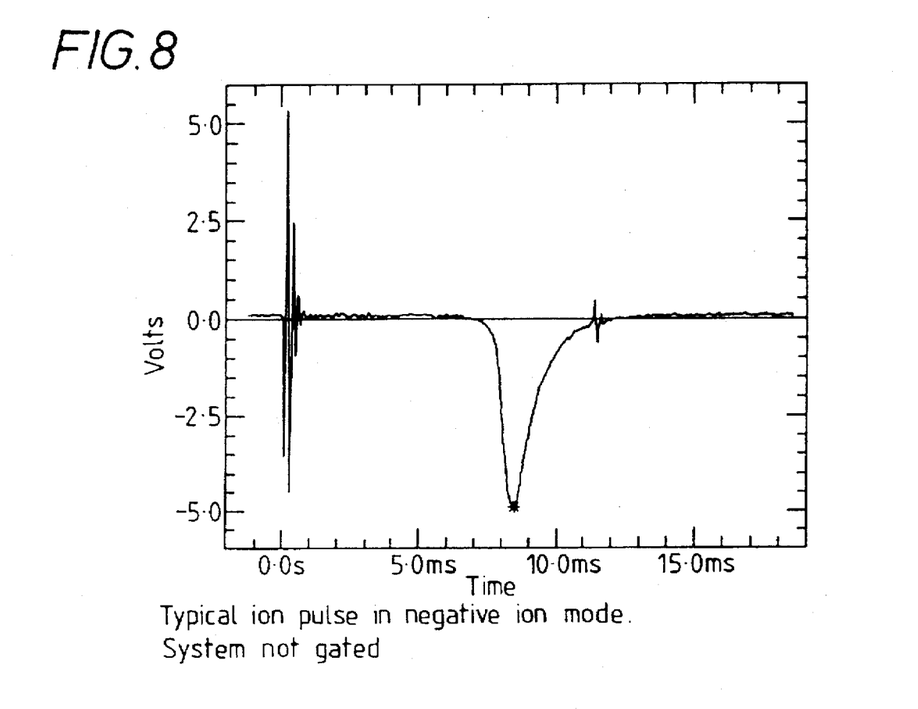

Typical ion pulses for the positive and negative modes with gate electrode 44 inoperative are shown in FIGS. 7 and 8 respectively.

Figure 9:
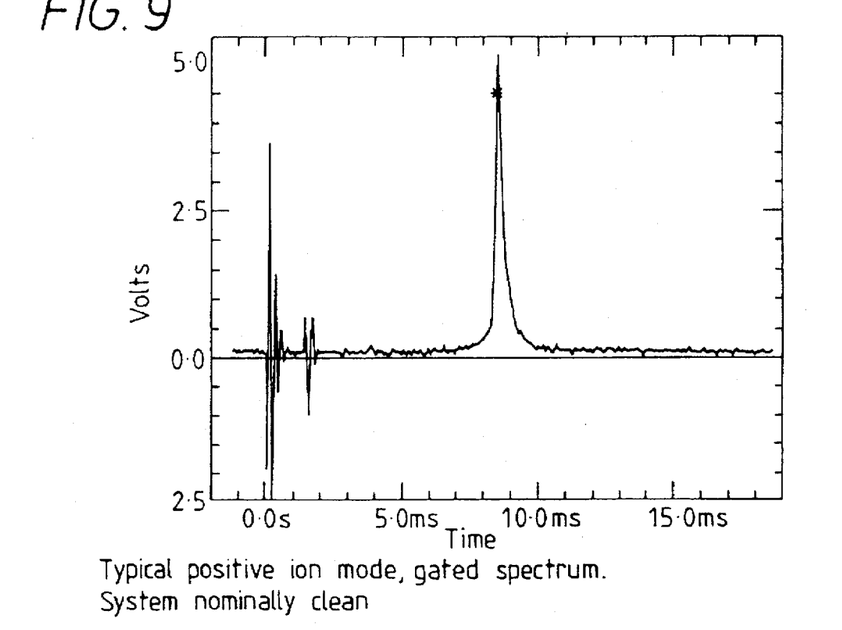
Figure 10:
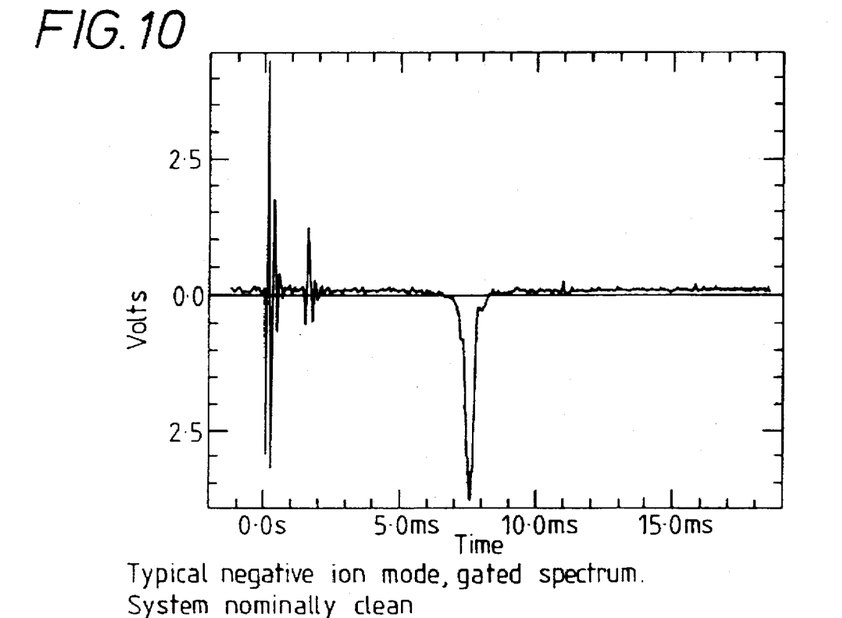

By gating a fraction of the ion pulses produced under the conditions described, into the drift region 30, spectra such as those shown in FIGS. 9 and 10 were produced, which are substantially similar in appearance to standard spectra produced using a Nickel-63 ionization source.

To allow for time taken for the ion pulse produced to traverse the reaction region 36 between the source 38 and the gate 44 a delay may be introduced between initiating the corona and opening the gate 44. By varying the length of the delay, the relative amplitudes of different ion peaks may be observed to alter in the ion mobility spectra. This effect was even more marked when a vapour producing monomer and dimer product ions was introduced into the reaction region.

It is believed that this effect is due to ion mobility separation occurring in the space between the source 38 and the gate 44, effectively enabling a primary separation of ion groups to take place in the reaction space, prior to further separation in the drift tube 30. This double separation means that the assembly is acting as a tandem or two-stage separation device, permitting greater ion selectivity to be achieved.

Use of a molybdenum wire corona point required a higher DC and pulse voltage to strike the corona and gave rise to a negative mode reactant ion peak (RIP) consisting of at least two ion species. The peak height ratio between the two species was varied by varying the applied voltage, implying that the ion chemistry of the corona discharge was being varies by electrical means. By experiment it was shown that if the faster RIP was made dominant by increasing the applied voltage, the response of the ion mobility spectrometer to the negative mode sample vapour was marked decreased, recovering when the slower RIP was made dominant, in effect providing the possibility of selectivity and sensitivity control of the ion mobility spectrometer by control of the corona voltage.

Figure 11:
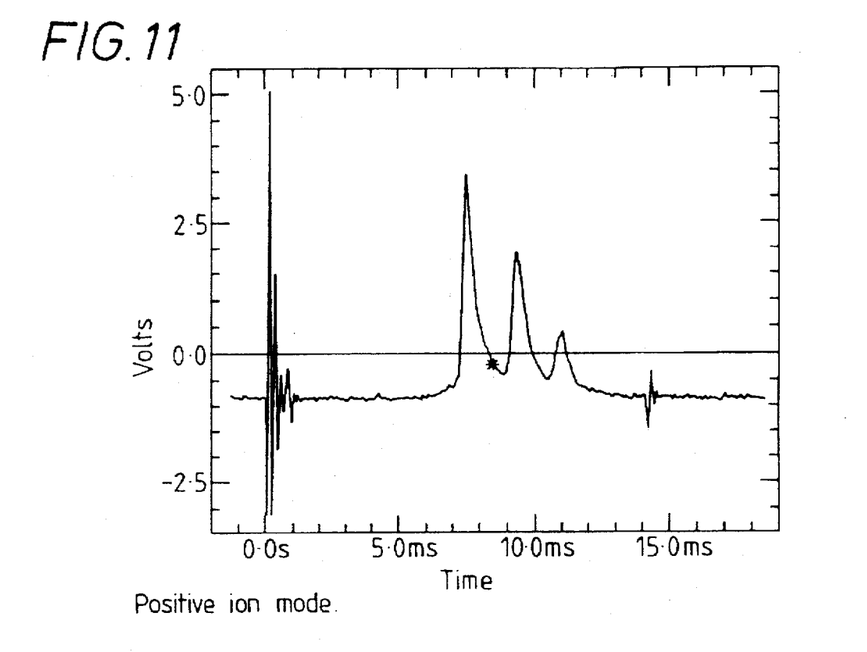
Figure 12:
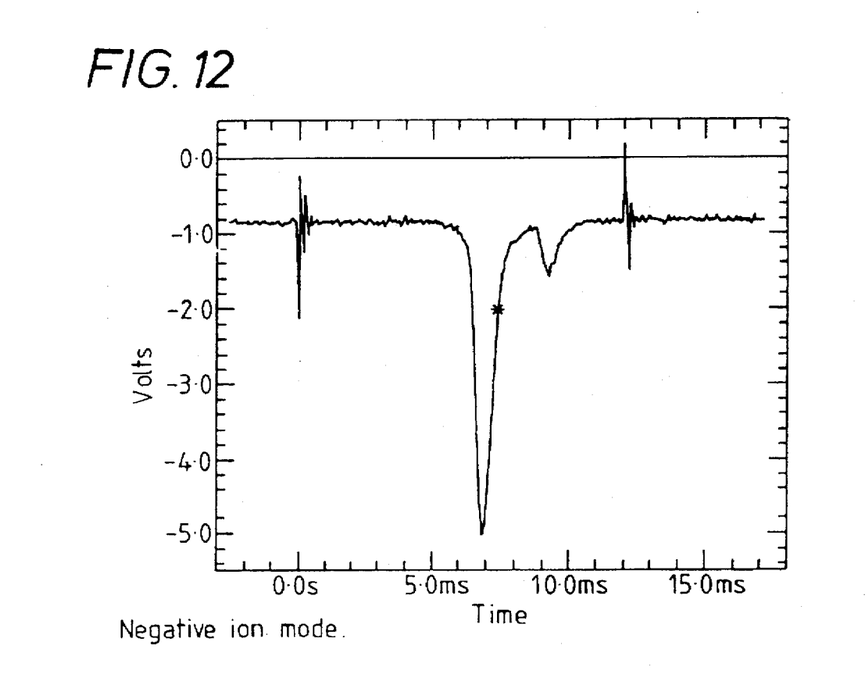

FIGS. 11 and 12 respectively show positive and negative ion spectra produced using the apparatus of FIG. 3 with the gate 44 inoperative (open) and conditions established for the operation of corona discharge ionization source 36 to produce an ion pulse as nearly narrow as that achieved by use of the gate 44.

This was achieved by igniting the corona discharge rapidly, delivering as little energy to the discharge as possible, and subsequently stopping the discharge as rapidly as possible.

The conditions which produced the spectra were:
FIG. 11: +2.7 kV DC plus +2.7 kV pulse; and
FIG. 12: −2.0 kV DC plus −260V pulse.

As it has been found that it is easier to strike a negative corona discharge, the negative reactant ion pulse is broader than the positive one, and hence more energy is delivered to the discharge. The spectrum of FIG. 12 was obtained with a resistor of 100 Kohm in series with the discharge, limiting the discharge current, possibly acting in conjunction with stray capacitances to damp the initiating pulse to the discharge.

Figure 13:
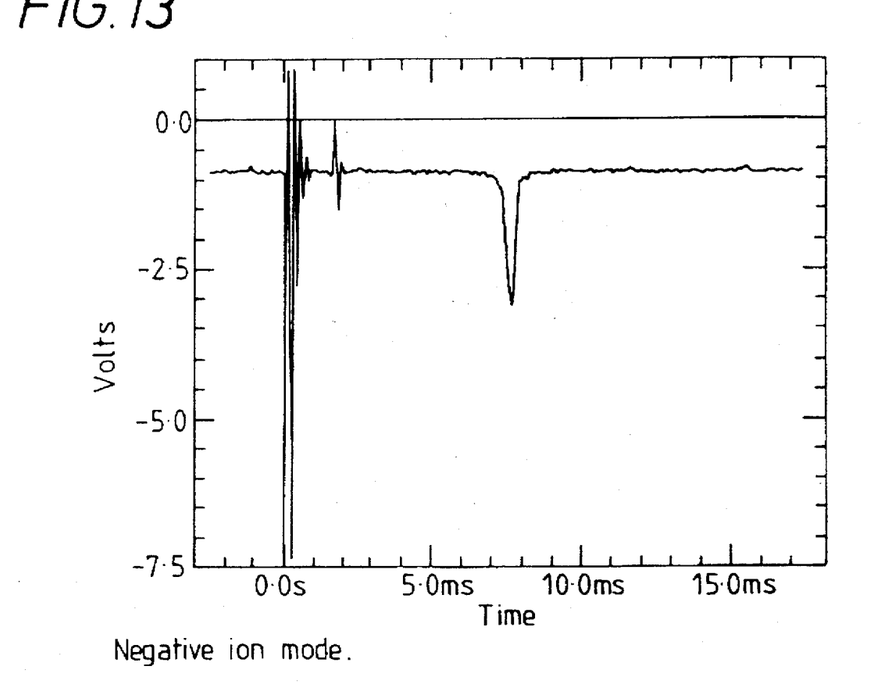

FIG. 13 illustrates a negative mode ion pulse produced using a different corona position with the DC potential of −1.54 kV applied to source 36, near the corona discharge threshold, and the applied pulse voltage low at −900 V.

Although run in this manner the source 36 produced some intermittent pulses which were long and irregular, others were as shown in FIG. 13 indicating a resolution from the apparatus comparable to that obtained from a gated system with the gate 44 in operation.

Running the apparatus in this manner removes the need for the complicated gate electrode structure, for the bias potential necessary to operate it and the electronic circuitry necessary to control it, making possible a simpler and less expansive construction of ion mobility spectrometer.

Figure 14:
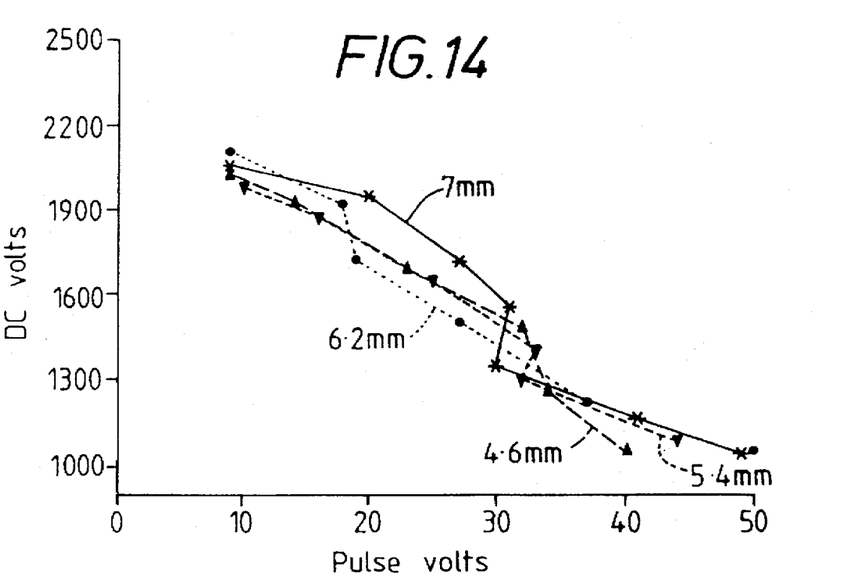
FIG. 14 is a plot of standing DC voltage against applied pulse voltage for the corona ionization source of FIG. 1, for various lengths of discharge gap.

FIG. 14 shows plots of DC potential against pulse voltage needed to strike a stable corona discharge in the negative mode for corona gap dimensions between 4.6 mm and 7 mm. The DC voltage values are absolute and include a component of approximately 1 kV to compensate for a standing voltage of the same value (present for other reasons) on the target electrode of the test instrument.

The plots show that with a very low DC potential difference between the two electrodes of the source, a stable corona discharge may be obtained with higher pulse voltages, meaning that the source could be operated, and ionization achieved without use of a standing DC potential on the corona point electrode relative to the target electrode, making possible further simplification of the ion mobility spectrometer.

Two further ionization source embodying the present invention will now be described with reference to FIGS. 15 and 16, and with reference to FIGS. 17 and 18, respectively.

Figure 15:
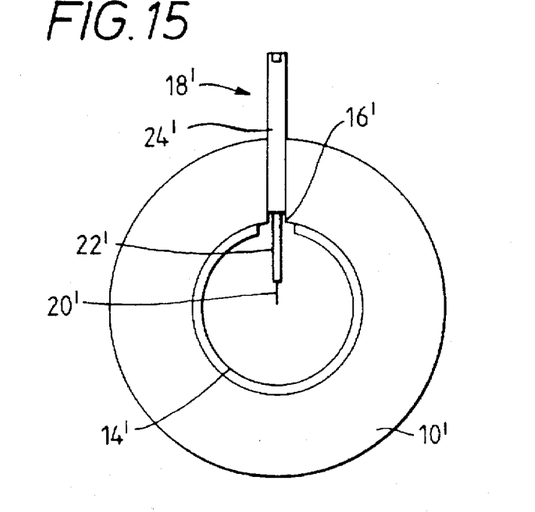
FIG. 15 is a plan view of an alternative ionization source embodying the present invention.
Figure 16:
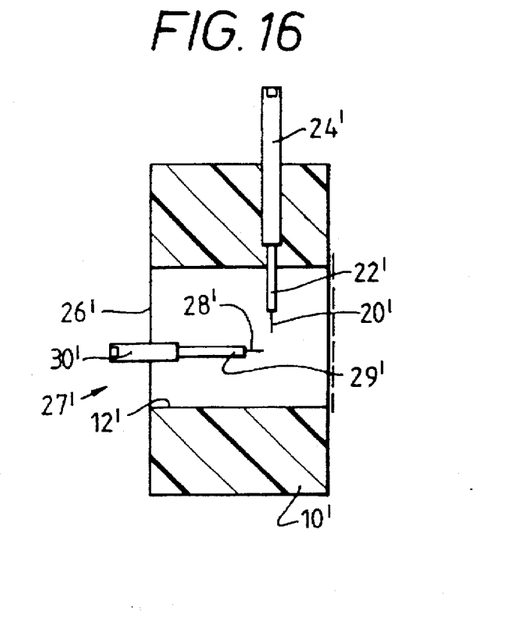
FIG. 16 is a sectioned side view of the source of FIG. 15.

Referring first to FIGS. 15 and 16, a corona discharge source in accordance with another embodiment of the invention consists of an annular body 10' of PFTE with an outer diameter of 30 mm, an inner diameter of 14 mm and a length of 15 mm.

The inner wall 12' of the body 10' carries a target electrode 14' of gold-plated brass with a longitudinal gap 16' through which a primary corona discharge point electrode assembly 18' projects.

The assembly 18' comprises a primary corona point 20', a conductive rod 22' and a carrier 24' which mounts the assembly in the wall of the annular body 10' and permits adjustment of the discharge gap between the corona point 20' end target electrode 14'.

One end 26' of the annular body 10' is closed and mounts an assembly 27', similar in construction to the assembly 18', comprising a secondary corona point 28', a conductive rod 29' and a carrier 30'.

Electrical connections (not shown) are made to the primary and secondary corona points 20 and 28 respectively, and to the target electrode 14.

Various materials may be employed for the corona points 20' and 28'. In one ionization source in accordance with the embodiment of the invention described with reference to FIGS. 15 and 16 the primary corona point 20' is a gold wire of 10 microns diameter, end the secondary corona point 28' a gold wire also of 10 microns diameter, although it will be understood that other materials may be used, and other dimensions, for primary and secondary corona points.

In operation, a primary corona discharge is established upon the primary corona point 20' by the application to it of an appropriate potential. As previously described, that potential may be positive or negative with reference to the target electrode 14' and may be steady, or may be pulsed, with or without a standing DC potential upon the point 20'. A steady potential of opposite sign to that applied to the primary corona point is 20' is applied to the secondary corona point 28' from a suitable source (not shown) permitting the potential upon secondary corona point 28' to be varied. This enables the quantity of ions generated by the primary corona discharge to be further controlled (the primary means of control being the amplitude and duration of the potential applied to the electrode 20') and the degree of suitability of the primary corona discharge of the point 20' also to be controlled.

Figure 17:
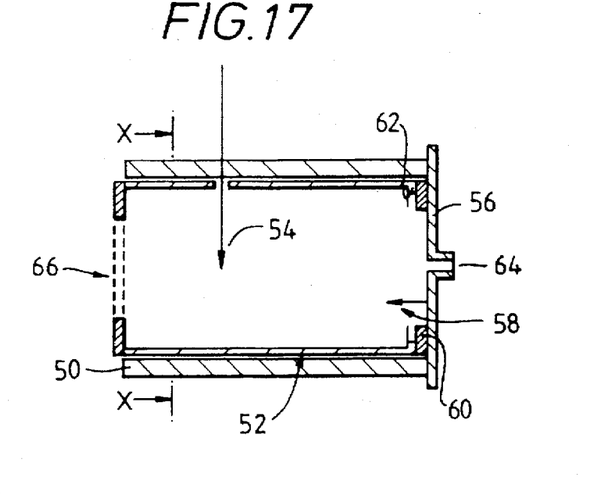
FIG. 17 is a side view of another alternative ionization source embodying the present invention.
Figure 18:
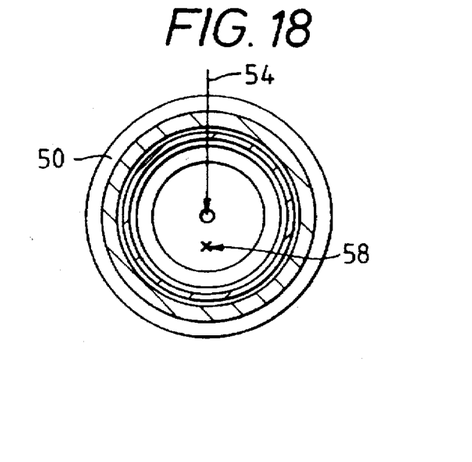
FIG. 18 is a sectioned end view in the direction of the arrows x—x of FIG. 17.

A further corona ionization source embodying the invention is shown in FIGS. 17 and 18 which incorporates a further electrode in the region of the secondary discharge point.

Referring to FIGS. 17 and 18, the corona ionization source comprises a cylindrical body 50, containing a target electrode 52. A primary corona point 54, shown diagrammatically, projects into the space within the body 50. One end of the body 50 is closed by a structure comprising an insulating disc 56 which mounts a secondary corona point 58 (again shown diagrammatically) an annular electrode 60, and an annular insulator 62. The disc 56 is centrally apertured at 64 to permit the introduction of sample and carrier. The other end of the body 50 carries a gating structure 66, insulated from the target electrode 52, which in operation controls the ingress of ions generated by the corona discharge upon corona point 54, from the source body 50 into the associated instrument, as described with reference to FIG. 3.

In operation, the annular electrode 60 carries a potential of opposite polarity to the potential applied to the secondary corona point 58.

In one example, where (for reasons associated with the potentials required for operation of the associated ion mobility spectrometer) the ion mobility gating structure 66 was held at +800 volts, the target electrode 52 was held at +1000 volts the primary corona point 54 was run at +1300 volts DC with pulses of +3000 volts applied to it, the annular electrode 60 was run at +750 volts and the secondary corona point 58 at 0 volts to − 200 volts.

If it were to be required to operate the corona ionization source with the target electrode 52 at zero potential, appropriate modification would require to be made to the potentials applied to the other electrodes in order to maintain the same potential differences between them. Similarly, if the primary corona point 54 is required for instrumental reasons to operate at a negative potential, the potentials on all the other electrodes will be appropriately modified.

Both of the embodiments of FIGS. 15 to 18 may be used in the Ion Mobility Spectrometer illustrated in FIGS. 2.

It will be appreciated that various modifications and adaptations may be made to corona discharge sources in accordance with the present invention without exceeding the scope of the invention.

We claim:

1. An ion mobility spectrometer comprising a sample introduction chamber into which sample material is introduced, a reaction chamber, a corona discharge ionization source provided in the reaction chamber for ionizing the sample material, a drift tube into which ionized sample material is passed, a collector electrode, a gating grid and a series of electrodes provided in the drift tube to draw ionized sample material toward the collector electrode, and a detecting unit for detecting ionized sample material reaching the collector electrode wherein the improvement comprises said corona discharge ionization source comprising a corona discharge electrode, said corona discharge electrode includes the distal end of a point electrode, a target electrode and means for applying a potential difference between the corona discharge electrode and the target electrode in order to establish a corona discharge between the two electrodes, said potential difference further comprises a substantially constant component, not of itself sufficient to cause corona discharge, plus a pulsed component, thereby ionizing material introduced into the region of the discharge.

2. An ion mobility spectrometer as claimed in claim 1 in which the pulsed component has both positive going and negative going portions with respect to the constant component.

3. An ion mobility spectrometer as claimed in claim 2 including means for adjusting the pulse frequency.

4. An ion mobility spectrometer as claimed in claim 2 including means for adjusting the pulse amplitude.

5. An ion mobility spectrometer as claimed in claim 2 including means for adjusting the pulse frequency and amplitude.

6. An ion mobility spectrometer as claimed in claim 1 in which the target electrode is generally cylindrical and surrounds the corona discharge electrode.

7. An ion mobility spectrometer as claimed in claim 1 in which the point electrode extends transversely of a longitudinal axis of the target electrode.

8. An ion mobility spectrometer as claimed in claim 1 in which the corona discharge electrode is mounted to an adjustable holder, whereby the position of the corona discharge electrode may be varied with respect to the target electrode.

9. An ion mobility spectrometer as claimed in claim 8 including a further corona discharge electrode and means for applying a potential to said discharge electrode.

10. An ion mobility spectrometer as claimed in claim 9 wherein a substantially constant potential is applied to the further corona discharge electrode.

11. An ion mobility spectrometer as claimed in claim 10 wherein the potential applied to the further corona discharge electrode is of opposite sign to the potential applied to the corona discharge electrode, with respect to the potential of the target electrode.

12. An ion mobility spectrometer as claimed in claim 11 in which the further corona discharge electrode includes the distal end of a point electrode.

13. An ion mobility spectrometer as claimed in claim 12 in which the point electrode comprising the further corona discharge electrode extends generally parallel with the longitudinal axis of the target electrode.

14. An ion mobility spectrometer as claimed in claim 13 including a counter electrode in the vicinity of the further corona discharge electrode and means for applying a potential to the counter electrode.

15. An ion mobility spectrometer as claimed in claim 14 in which the potential applied to the counter electrode is of opposite sign to the potential applied to the further corona discharge electrode, with respect to the potential of the target electrode.

16. An ion mobility spectrometer as claimed in claim 15 in which the counter electrode is annular.

17. An ion mobility spectrometer as claimed in claim 16 in which the counter electrode at least partially surrounds the further corona discharge electrode.

18. An ion mobility spectrometer as claimed in claim 1 incorporating gating means arranged selectively to allow ions formed within the region of the discharge from migrating away from the source.

19. An ion mobility spectrometer as claimed in claim 1 incorporating gating means arranged selectively to prevent ions formed within the region of the discharge from migrating away from the source.

20. An ion mobility spectrometer as claimed in claim 1 including an ion gate and means for operating the gate a predetermined time after initiation of a corona discharge.

21. An ion mobility spectrometer as claimed in claim 20 including control means arranged to vary said predetermined time.

22. An ion mobility spectrometer as claimed in claim 1 further comprising a semi-permeable ·membrane and in which said sample introduction chamber and said reaction chamber are separated by said semi-permeable membrane.

* * * * *